United States Patent [19]
Nicholas et al.

[11] Patent Number: 5,349,109
[45] Date of Patent: Sep. 20, 1994

[54] MOLYBDENUM-CATALYZED AMINATION OF OLEFINS

[75] Inventors: Kenneth M. Nicholas, Norman, Okla.; Anurag S. Srivastava, Newark, Del.

[73] Assignee: The Board of Regents of the University of Oklahoma, Norman, Okla.

[21] Appl. No.: 112,908

[22] Filed: Aug. 26, 1993

Related U.S. Application Data

[63] Continuation of Ser. No. 710,219, Jun. 4, 1991, abandoned.

[51] Int. Cl.$^5$ ............................................. C07C 209/60
[52] U.S. Cl. ..................................... 564/408; 502/211; 502/220; 502/321; 534/572; 534/751; 534/843; 560/24; 560/29; 560/157; 560/160; 560/170; 560/172; 560/193; 560/196; 560/250; 560/251; 560/253; 564/47; 564/58; 564/59; 564/60; 564/153; 564/156; 564/160; 564/163; 564/164; 564/199; 564/215; 564/219; 564/305; 564/336; 564/342; 564/343; 564/374; 564/383; 564/396; 564/431; 564/471; 564/485; 564/502; 564/509
[58] Field of Search ............... 564/343, 408, 485, 509, 564/383, 198, 305, 431; 502/211, 220, 321; 560/255, 250; 534/572, 751, 843

[56] References Cited

U.S. PATENT DOCUMENTS

| | | | |
|---|---|---|---|
| 2,571,099 | 10/1951 | Arthur, Jr. et al. | 260/465.3 |
| 2,904,580 | 9/1959 | Idol, Jr. | 260/465.3 |
| 3,017,435 | 1/1962 | Coffman et al. | 564/485 |
| 3,044,966 | 7/1962 | Callahan et al. | 252/437 |
| 3,062,886 | 11/1962 | Pritchett et al. | 564/485 |
| 3,156,729 | 11/1964 | Mador et al. | 564/485 |
| 3,496,215 | 2/1970 | Drinkard et al. | 260/465.8 |
| 3,502,725 | 3/1970 | Dewhirst et al. | 260/577 |
| 3,956,180 | 5/1976 | Cavitt | 252/431 |
| 4,091,019 | 5/1978 | Keppel et al. | 564/485 |
| 4,100,194 | 7/1978 | Hobbs et al. | 564/408 |
| 4,107,079 | 8/1978 | Chevallier et al. | 564/485 |
| 4,171,313 | 10/1979 | Mares et al. | 260/343 |
| 4,204,997 | 5/1980 | Hobbs et al. | 564/408 |
| 4,302,603 | 11/1981 | Pez | 564/485 |
| 4,317,932 | 3/1982 | Jachimowicz | 564/408 |
| 4,596,785 | 6/1986 | Toulhoat et al. | 502/220 |
| 4,845,068 | 7/1989 | Takahashi et al. | 502/211 |

FOREIGN PATENT DOCUMENTS

| | | |
|---|---|---|
| 2203710 | 8/1972 | Fed. Rep. of Germany . |
| 2733516 | 2/1978 | Fed. Rep. of Germany . |
| 1178812 | 1/1970 | United Kingdom . |

OTHER PUBLICATIONS

Sharpless et al., *J. Am. Chem. Soc.*, vol. 98, pp. 269–271 (1976).

Sharpless et al., *J. Org. Chem.*, vol. 41 (1), pp. 176–177 (1976).

Liebeskind et al., *J. Am. Chem. Soc.*, vol. 100 (22), pp. 7061–7063 (1978).

Muccigrosso et al., *J. Am. Chem. Soc.*, vol. 100 (22), pp. 7063–7065 (1978).

*Primary Examiner*—Richard L. Raymond
*Assistant Examiner*—Scott C. Rand
*Attorney, Agent, or Firm*—Dunlap Codding Lee

[57] ABSTRACT

A process for making unsaturated α-amines from olefins wherein the process includes adding an aminating agent, an olefin and a molybdenum based catalyst to a reaction vessel having a nitrogen atmosphere. The catalyst may be described by the general formula LL'MoO$_2$, L$_2$L'MoO$_2$, or LL'MoO(X-Y).

15 Claims, No Drawings

MOLYBDENUM-CATALYZED AMINATION OF OLEFINS

This is a continuation of copending application Ser. No. 07/710,219 filed Jun. 4, 1991, now abandoned.

FIELD OF THE INVENTION

This invention relates to a process for making unsaturated α-amines from olefins. More particularly, but not by way of limitation, the invention comprises a process wherein an aminating agent, an olefin and a molybdenum based catalyst are added to a reaction vessel.

The present invention includes a process comprising the steps of placing an olefin, a catalyst having the general formula LL'MoO$_2$, L$_2$L'MoO$_2$ or LL'MoO(X-Y) and an aminating agent in a reaction vessel to produce an αamine. The present invention also further comprises a method wherein a solvent is placed in the reaction vessel with the olefin and catalyst.

BACKGROUND OF THE INVENTION

The direct production of organonitrogen compounds from hydrocarbons remains an attractive but largely elusive goal. It has been particularly difficult to produce allylic or α-amines with a high degree of regioselectivity.

The few reports of ammoxidation reactions of olefins are stoichiometric and typically involve reactions of imido compounds as aminating agents. Imido compounds are difficult to prepare, unstable aminating agents and have a high toxicity. In addition, with imido compounds there are limited options for -NR variation. Thus, the use of imido compounds has little utility in large scale preparation of allyl amines of diverse types.

Another method for preparing allylic amines utilizes displacement reactions. This type of reaction uses displacement of the corresponding electrophiles (e.g. allylhalides) by amines and are thus indirect routes, requiring two or more steps from the hydrocarbon. In addition, regio- and stereoselectivity is problematic with this type of reaction, especially in the initial introduction of the heteroatomic leaving group.

DESCRIPTION OF THE PREFERRED EMBODIMENTS

The present invention comprises a process for making unsaturated α-amines (i.e. allylamines) of the general formula R-C=C—C(NR)R$_2$ from compounds of unsaturated hydrocarbons having one or more double bonds, which may be generally referred to as olefins. The invention comprises the use of a molybdenum catalyst to promote the site specific addition of a nitrogen compound onto the olefin's α-carbon.

The reaction may be represented by the formula:

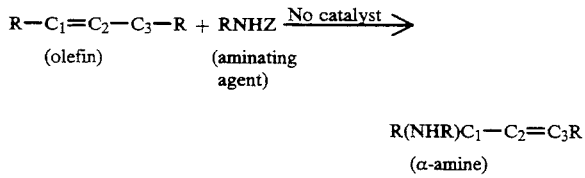

The olefin may be any compound having a carbon-carbon double bond and an α-carbon wherein the α-carbon has a hydrogen atom bonded thereto. Since one of the advantages of this reaction is its regioselectivity, the a-hydrogen is necessary to provide a substitution site for the aminating agent. The R as used in this specification represents a hydrogen or any organic group, such as an alkyl, an aryl, a carbonyl, a carboalkoxy or a carboxamido.

The aminating agent is an amine which may be represented by the general formula RNHZ. The aminating agent has a suitable leaving group Z such as hydroxyl (—OH), alkoxy (—OR), halo (F, Cl, Br or I), sulfonate ester (—SO$_3$R) alkyl, aryl, carbonyl (—C(=O)R), carboalkoxy (—CO$_2$R) and carboxamido (—C(=O)NR$_2$). Thus, suitable agents include hydroxylamines, haloamines, N-hydroxyurethanes, and hydroxamic acids.

The catalyst may have the general formula L$_n$MoO$_{1,2}$ wherein the molybdenum has an oxidation state from IV to VI and more preferably an oxidation state of VI.

One preferred molybdenum catalyst may be represented by the formula L$^{di}$L'MoO$_2$ where the L$^{di}$ is a dianionic ligand such as an amino dicarboxylate or an amino diphenolate. An example of an amino dicarboxylate is pyridine 2, 6-dicarboxylate. An example of an amino diphenolate is N-( salicylidene )-2-hydroxybenzeneamine. In the above catalyst, L' is generally a neutral oxygen, nitrogen or sulfur donor and may include water, alcohols, ethers, ketones, esters, amides, nitroalkanes, sulfoxides, nitriles, phosphoric acid triamides, or sulfones.

Another preferred molybdenum catalyst may be represented by the formula L$_2^{mono}$L'MoO$_2$. With this catalyst the L$^{mono}$ is a monoanionic ligand. Examples of monoanionic ligands include carboxylates, α-amino carboxylates, pyridine 2-carboxylates, β-diketonates, dithiocarbamates and Schiff bases such as salicylaldimine. With this catalyst the L' may be a neutral donor as above or may be absent from the molecule altogether.

Yet another preferred molybdenum catalyst may be represented by the formula LL'MoO(X-Y). With this catalyst the L may be a dianionic ligand or a monoanonic ligand both of which are described above. The L' is a neutral donor such as described above and the X-Y is a peroxo (O-O) or a nitroso (RN-O) ligand.

It may be desirable to use a solvent in some instances. For example, if the olefin is in a solid state at the chosen reaction temperature the use of a solvent would be necessary. Appropriate solvents include hydrocarbons, ethers, halogenated alkanes, esters, amides, sulfoxides, nitriles, nitroalkanes and phosphoric acid triamides. However, solvents which would react with the catalyst and thereby destroy it or enter into side reactions should not be used. Examples of inappropriate solvents are ketones and primary amines.

In performing the process of this invention the olefin and the catalyst are placed in a reaction vessel preferably having a nitrogen atmosphere. It is not important which is added first. The catalyst may theoretically comprise a single molecule. However, it has been found that when about 1-10 mole% of the solution is catalyst the reaction proceeds at an economical rate. The catalyst should be in solution, if the olefin is in solid form it should be heated and/or a solvent should be added to dissolve the olefin. Preferably the aminating agent is added to the olefin/catalyst solution. More preferably the aminating agent is added slowly thereby suppressing significant formation of aminating agent byproducts. In a reaction vessel containing about 15 ml of olefin/- catalyst solution the aminating agent may be added dropwise without undesirable side reactions. It should be understood from the foregoing that the aminating agent may be added at a much greater rate to a solution having a larger volume.

The reaction temperature range is from about 0° C. to about 200° C., and preferably the temperature is maintained between 20° C. and 100° C.

The invention is illustrated by the following examples.

Example 1

A stirred mixture containing dioxane (12 mL), 3 mL (54mmol) of 2-methyl-2-hexene, 1g of 4A Molecular Sieves, and 0. 051 g ( 0.11mmol ) of ( 2,6-dipicolinato )$MoO_2$(hexamethyl phosphoramide ) is heated at reflux (ca. 100° C.) under a nitrogen atmosphere while a toluene solution ( 50 mL ) of N-phenyl hydroxylamine ( 1.26g, 11.6 mmol) is added dropwise over a 24 hr period. After heating an additional 6–12 hr, the mixture was allowed to cool and the volatiles were removed by evaporation at reduced pressure and the residue chromatographed over silica gel. Elution with pentane afforded phenyl 3-(2-methyl-1-hexenyl) amine (>95% one isomer by NMR, GC/MS) in 20–30% yield based on the hydroxylamine. Later fractions contained aniline, azobenzene and azoxybenzene.

Example 2

A stirred mixture containing dioxane (12mL), 3 mL of 1-octene, 1g of 4A Molecular Sieves, and 0.051 g (0.11 mmol) of (2,6-diPicolinato)$MoO_2$(hexamethyl phosphoramide)is heated at reflux (ca. 100° C.) under a nitrogen atomosphere while a toluene solution (50 mL)of N-phenyl hydroxylamine (1.26 g, 11.6 mmol) is added dropwise over a 24 hr period. After heating an additional 6–12 hr, the mixture was allowed to cool and the volatiles were removed by evaporation at reduced pressure and the residue chromatographed over silica gel. Elution with pentane afforded phenyl trans-2-octenyl amine (>95% one isomer by NMR, GC/MS) in 20–30 % yield based on the hydroxylamine. Later fractions contained aniline, azobenzene and azoxybenzene.

Example 3

A stirred mixture containing dioxane (12 mL), 3 mL of cyclohexene, 1g of 4A Molecular Sieves, and 0.11 mmol of (2,6-dipicolinato)(HMPA)MoO(O) (ONPh) is heated at reflux (ca. 100° C.) under a nitrogen atmosphere while a toluene solution (50 mL) of N-phenyl hydroxylamine (1.26 g, 11.6 mmol) is added dropwise over a 24 hr period. After heating an additional 12–24 hr, the mixture was allowed to cool and the volatiles were removed by evaporation at reduced pressure. Chromatography of the residue over silica gel and elution with pentane afforded phenyl 3-cyclohexenyl amine (>95% one isomer by NMR, GC/MS) in 15–25% yield based on the hydroxylamine. Later fractions contained aniline, azobenzene and azoxybenzene.

We claim:

1. A process for making unsaturated α-amines from olefins wherein the α-amines have a base chain of carbon atoms having the same number of carbon atoms as the olefin, comprising:

placing a liquid olefin having at least three carbons and an α-hydrogen; a catalyst having the general formula LL'MoO(X-Y) wherein L is selected from a group consisting of monoanionic ligands, and dianionic ligands, L' is a neutral oxygen, nitrogen, or sulfur neutral donor and X-Y is selected from a group consisting of, a peroxo ligand or a nitroso ligand; and an aminating agent having the general formula RNHZ wherein Z is selected from a group consisting of,
a hydroxyl,
an alkoxy,
a halo, and
a sulfonate ester, and
wherein R is selected from a group consisting of,
a hydrogen,
an alkyl,
an aryl,
a carbonyl
a carboalkoxy or
a carboxamido,
in a reaction vessel.

2. The process of claim 1 wherein the reaction vessel contains a nitrogen atmosphere.

3. The process of claim 2 wherein the liquid olefin and the catalyst are added to the reaction vessel before the aminating agent.

4. The process of claim 3 wherein the reaction vessel is maintained at a temperature of between 20° and 100° Centigrade during the reaction.

5. The process of claim 3 wherein L' is selected from a group consisting of
water
alcohols,
ethers,
esters,
ketones,
amides,
nitroalkanes,
sulfoxides,
sulfoes,
nitriles and
phosphoric acid triamides.

6. The process of claim 3 wherein the aminating agent is added at a rate wherein significant formation of aminating agent byproducts is suppressed.

7. The process of claim 3 wherein L is selected from a group consisting of amino dicarboxylates, amino diphenolates, dithiocarbamates and carboxylates.

8. A process for making unsaturated α-amines comprising:

placing an olefin having at least three carbons and an α-hydrogen; a solvent; a catalyst with the general formula LL'MoO(X-Y) where L is selected from a group consisting of a monoanionic ligand and a dianionic ligand, L' is a neutral oxygen, nitrogen, or sulfur donor, and X-Y is selected from a group consisting of, a peroxo ligand, or a nitroso ligand; and an aminating agent having the general formula RNHZ wherein Z is selected from a group consisting of,
a hydroxyl,
an alkoxy,
a halo, and
a sulfonate ester, and
wherein R is selected from a group consisting of,
a hydrogen,
an alkyl,
an aryl,
a carbonyl
a carboalkoxy or
a carboxamido,
in a reaction vessel.

9. The process of claim 8 wherein the reaction vessel contains a nitrogen atmosphere.

10. The process of claim 9 wherein the liquid olefin and the catalyst are added to the reaction vessel before the aminating agent.

11. The process of claim 10 wherein the solvent is an organic solvent selected from a group consisting of hydrocarbons, ethers, halogenated alkanes, esters, amides, sulfoxides, nitriles, nitroalkanes, and phosphoric acid triamides.

12. The process of claim 10 wherein the reaction vessel is maintained at a temperature of between 20° and 100° Centigrade during the reaction.

13. The process of claim 10 wherein L' is selected from a group consisting of:
water
alcohols,
ethers,
esters,
ketones,
amides,
nitroalkanes,
sulfoxides,
sulfones,
nitriles and
phosphoric acid triamides.

14. The process of claim 10 wherein the aminating agent is added at a rate wherein significant formation of aminating agent byproducts is suppressed.

15. The process of claim 10 wherein L is selected from a group consisting of amino dicarboxylates, amino diphenolates, dithiocarbamates and carboxyiates.

* * * * *

UNITED STATES PATENT AND TRADEMARK OFFICE
CERTIFICATE OF CORRECTION

PATENT NO. : 5,349,109
DATED : September 20, 1994
INVENTOR(S) : Nicholas et al.

It is certified that error appears in the above-identified patent and that said Letters Patent is hereby corrected as shown below:

Column 1, line 15, after "LL'MoO$_2$" please delete "." and replace with --,--.

Column 1, line 17, please delete "αamine" and replace with --α-amine--.

Column 2, line 19, please delete "L$^{dl}$" and replace with --L$^{di}$--.

Signed and Sealed this

Fourteenth Day of February, 1995

Attest:

BRUCE LEHMAN

Attesting Officer     Commissioner of Patents and Trademarks